United States Patent [19]
Nanba et al.

[11] Patent Number: 5,830,486
[45] Date of Patent: Nov. 3, 1998

[54] COSMETIC

[75] Inventors: Tomiyuki Nanba; Kazunori Yamazaki, both of Yokohama, Japan

[73] Assignee: Shiseido Company, Ltd., Tokyo, Japan

[21] Appl. No.: 867,776

[22] Filed: Jun. 3, 1997

[30] Foreign Application Priority Data

Jun. 4, 1996 [JP] Japan ..................................... 8-163755

[51] Int. Cl.⁶ ....................................................... A01K 7/48

[52] U.S. Cl. ............................... 424/401; 424/61; 424/63; 424/64; 424/101; 424/70.12; 424/70.121; 424/78.03; 424/78.08; 514/63; 556/450; 556/456; 556/461

[58] Field of Search ................................ 424/401, 70.12, 424/70.121, 61, 63, 64, 70.1, 78.03, 78.08; 514/63; 556/450, 456, 461

[56] References Cited

U.S. PATENT DOCUMENTS 5,714,134  2/1998  Richard et al. ........................... 424/59

*Primary Examiner*—Jyothsna Venkat
*Attorney, Agent, or Firm*—Townsend & Banta

[57] ABSTRACT

A cosmetic which contains perfluoroalkyl denatured methylphenyl polysiloxane with a structure represented by the following general formula (I):

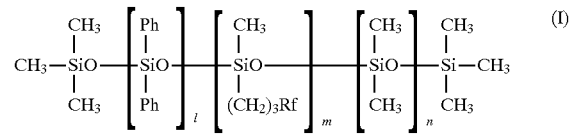

where l, m and n denote average numbers where l is 1–150, m is 1–150 and n is 0–150, a denotes an integer 0–10, and Rf denotes a perfluoroalkyl group with a carbon number of 1–12.

1 Claim, No Drawings

COSMETIC

RELATED APPLICATION

This application claims the priority of Japanese Patent application No.8-163755 filed on Jun. 4, 1996, which is incorporeted herein by reference.

BACKGROUND OF THE INVENTION

1. Field of the Invention

This invention relates to a cosmetic which characteristically contains a specific perfluoroalkyl denatured methylphenyl polysiloxane, is superior in water resistance and sevum resistance, and has a long lasting cosmetic effect wherein it does not come off easily as a result of perspiration, kitchen work/washing, swimming. etc.

2. The prior Art

Conventionally skin cream and skin lotion have been used to protect the skin from rough dry skin conditions. They protect the skin by forming an oil barrier on the skin to prevent the loss of aqueous components, sevum, etc. in the skin due to perspiration, kitchen work/washing and such and also by endowing flexibility to the skin by means of humectants and aqueous ingredients.

Recently, since cream and lotion come off the skin by kitchen work/washing and perspiration, such products with a lasting effect which save the time of re-applying are desired. For this purpose, attempts have been made to increase the water resistance by adding silicone oil and silicone resin.

Makeup cosmetics including foundations and lipsticks have a problem in that the makeup comes off over time and that foundations and lipsticks adhere to clothes and lipsticks adhere to glasses. Because of this, such products with a lasting cosmetic effect and a secondary adhesion prevention effect are desired. For this purpose, attempts have been made to increase the water resistance by adding silicone oil and silicone resin.

Also, in the hair cosmetic field including hair mousse and hair sprays, the hair is set by hair setting resins. Here again silicon oil is added because products which hold the setting even under high humidity and has a lasting setting effect are desired.

However, although silicone oil and silicone resin which are used to improve these problems are effective in preventing makeup from coming off due to water and perspiration, they are not effective enough in preventing makeup from coming off due to oil such as sevum.

BRIEF SUMMARY OF THE INVENTION

The inventors conducted earnest research to address this problem and completed the present invention by discovering that a cosmetic which was sufficiently effective in preventing not only water and perspiration but also oil components such as sevum from washing off the makeup could be obtained by blending perfluoroalkyl modified methylphenyl polysiloxane with a specific structure.

The present invention provides a cosmetic which contains perfluoroalkyl denatured methylphenyl polysiloxane with a structure represented by the following general formula (I):

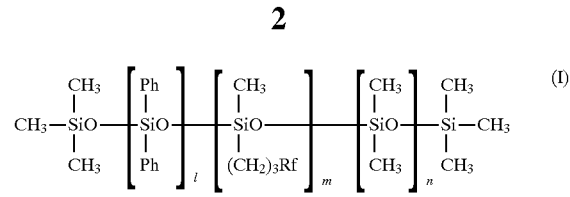

where l, m and n denote average numbers where l is 1–150, m is 1–150 and n is 0–150, a denotes an integer 0–10, and Rf denotes a perfluoroalkyl group with a carbon number of 1–12.

Silicone oil and silicon resin which have been used conventionally for the purpose of increasing the long lasting cosmetic effect have a high water resistance but do not necessarily have a high oil resistance, i.e. they are not sufficiently effective in terms of sevum resistance. The perfluoroalkyl denatured methylphenyl polysiloxane used in the present invention represented by the aforementioned general formula has an increased oil resistance without sacrificing water resistance by replacing some of the methyl groups of dimethyl polysiloxane with perfluoroalkyl groups. Also, solubility in other oil components is increased by replacing some of the methyl group with phenyl groups. Furthermore, phenyl groups increase the refractive index and thus improve the gloss. Therefore, a more glossy and long lasting cosmetic can be prepared by adding the present invention to lipsticks and hair care products.

Rf in the perfluoroalkyl denatured methylphenyl polysiloxane used in the present invention is a perfluoro group with a carbon number of 1–12 and may either be a linear chain or branched chain. Examples include trifluoromethyl, pentafluoroethyl, heptafluoropropyl, nonafluorobutyl, tridecafluorohexyl, heptadecafluorooctyl, 2-pentafluoroethyldodecafluorohexyl, $C_{10}F_{31}$ and $C_{17}F_{25}$. When perfluoroalkyl groups are long and m/l+m+n is large, the ratio of the fluorine group in the molecule becomes high and the water resistance and the oil resistance improve, but solubility in other oil components becomes poor. When 1/1+m+n is large, then the phenyl group content becomes high and solubility in other hydrocarbon oil components becomes high, the glossiness also improves. Selection of l, m, n and the perfluoro group in Rf depends on the degree of water resistance and oil resistance required of the product, solubility in other oil components used in the product, etc. These perfluoroalkyl denatured methylphenyl polysiloxanes can be obtained as commercial products.

The amount of perfluoroalkyl modified methylphenyl polysiloxane to be blended is typically 0.5–95 wt %, depending on the form of the cosmetic. To achieve a long lasting cosmetic effect, a preferable range is 3–50 wt %, and a more preferable range is 5–30 wt %.

In addition to the aforementioned essential ingredients, other ingredients which are typically blended into a cosmetic can be blended into the cosmetic of the present invention. Examples include various hydrocarbon oils, higher fatty acids, higher alcohols, esters, fat/oils, waxes, silicone and fluorine oil such as squalane, liquid paraffin, vaseline, microcrystalline wax, ozokerite, ceresin, myristic acid, palmitic acid, stearic acid, oleic acid, isostearic acid, behenic acid, cetyl alcohol, stearyl alcohol, oleyl alcohol, batyl alcohol, cetyl-2-ethylhexanoate, 2-ethylhexyl palmitate, 2-octyldedecyl myristate, neopentyl glycol-2-ethylhexanoate, glyceryl trioctancate, 2-octyldodecyl oleate, isopropyl myristate, myristyl myristate, glyceryl triisostearate, glyceryl trioleate, coconut oil fatty acid triglyceride, olive oil, avocado oil, jojoba oil, sunflower oil, safflower oil, tsubaki oil, shea butter, macadamia nut oil, mink oil, lanoline, castor oil, Japanese core wax, dimethyl polysiloxane, ring dimethyl polysiloxane, methylphenyl polysiloxane, silicone resin, polymer silicone, polyether modified silicone, amino denatured silicone, perfluoro polyether and perfluorocarbon, humectants such as ethylene glycol, diethylene glycol, 1,3-butylene glycol, glycerine, hexamethylene glycol, isoprene glycol, polyethylene glycol, propylene glycol, dipropylene glycol, diglycerine, polyglycerine, hyaluronic acid, sodium chondroitin sulfate, chitin and chitosan, ultraviolet light absorbents, antioxidants, preservatives, thickeners, drugs such as anti-inflammatories, vitamins, hormones and whitening agents, perfumes, pearl pigments such as talc, muscovite, synthetic mica, phlogopite, lepidolite, black mica, lithia mica, sericite, kaolin, titanium dioxide, titanium oxide-coated mica, titanium oxide-coated talc, titanium oxide-coated oxybismuth chloride, fish scale flakes and colored titanium oxide-coated mica, metal powder pigments such as aluminum powder and copper powder, inorganic pigments such as red iron oxide, yellow iron oxide, black iron oxide, carbon black, chrome oxide, chrome hydroxide, cobalt titanate, ultramarine blue, Berlin blue, zinc white, bentonite, barium sulfate, metal soap, silious earth, aluminum silicate, strontium silicate, metal salts of tungstic acid, calcium carbonate, magnesium carbonate, chrome oxide, chrome hydroxide, alumina, silica, hydroxyapatite, boron nitride and zeolite, organic powder such as nylon powder, PMMA powder, polystyrene powder, polyethylene powder, teflon powder, polyester powder and cellulose powder, organic pigments such as red 201, red 202, red 204, red 205, red 220, red 226, red 228, red 405, orange 203, orange 204, yellow 205, yellow 401 and blue 404, powder of organic pigments such as zirconium, barium or aluminum lakes of red 3, red 104, red 106, red 227, red 230, red 401, red 505, orange 205, yellow 4, yellow 5, yellow 202, yellow 203, green 3 and blue 1, and natural colors such as chlorophyll and β-carotene. Hair setting polymers including polyvinylpyrrolidone, PVP-VA, vinyl methyl ether-maleic anhydride copolymer, vinyl acetate-crotonic acid copolymer, polyvinylpyrrolidone N,N-dimethyl aminoethyl methacrylic acid copolymer diethyl sulfate solution, N-methacryloyloxyethyl-N,N-dimethyl ammonium-N-α-methylcarboxybetaine-alkyl methacrylate copolymer and vinylpyrrolidone-stearyl acrylate-stearoyloxyethyl-N,N-dimethylamine copolymer can also be blended in.

Also, needless to say, the cosmetic of the present invention can be made into a water-in-oil or oil-in-water type emulsion lipstick within the range where water repellency is maintained by blending purified water, water soluble ingredients and an appropriate surfactant and using an emulsification technique.

EXAMPLES

The present invention is further described in detail below by referring to examples. The present invention is not limited to these examples. The unit of the amount blended is always weight percent.

(Example 1 Cream)

| | |
|---|---|
| (1) Dimethyl polysiloxane (6 CS/25° C.) | 10.0% |
| (2) Perfluoroalkyl denatured methylphenyl polysiloxane (1 = 22, m = 20, n = 66, a = 3 and Rf = $c_8F_{17}$ in general formula (I)) | 20.0 |
| (3) Liquid paraffin | 6.5 |
| (4) Cetyl alcohol | 3.0 |
| (5) Glyceryl monostearate | 2.0 |

-continued (Example 1 Cream)

| | |
|---|---|
| (6) POE (20) sorbitan monooleate | 6.0 |
| (7) Purified water | 43.1 |
| (8) Glycerine | 4.0 |
| (9) 1,3-butylene glycol | 5.0 |
| (10) Preservative | 0.2 |
| (11) Perfume | 0.2 |

The materials (1)–(5) and (11) were mixed, heated and dissolved, and the temperature was kept at 70° C. to obtain the oil phase. Separately, the materials (6)–(10) were heated and dissolved, and the temperature was kept at 70° C. to obtain the water phase. The water phase was added to the oil phase and the mixture was thoroughly emulsified with an emulsifier. After the emulsification, the emulsion was cooled while being stirred. When the temperature became lower than 35° C., it was poured into a container and allowed to cool and harden to obtain the cream.

(Comparative example 1 Cream)

| | |
|---|---|
| Dimethyl polysiloxane (6CS 25° C.) | 10.0% |
| Dimethyl polysiloxane (100CS 25° C.) | 20.0 |
| Liquid paraffin | 6.5 |
| Cetyl alcohol | 3.0 |
| Glycerol monostearate | 2.0 |
| POE (20) sorbitan monooleate | 6.0 |
| Purified water | 43.1 |
| Glycerine | 4.0 |
| 1,3-butylene glycol | 5.0 |
| Preservative | 0.2 |
| Perfume | 0.2 |

The cream of Comparative example 1 was obtained using the same preparation method as Example 1.

(Effects)

Example 1 and Comparative example 2 were evaluated by a panel of 20 specialists. The water resistance was evaluated by a sensory test of how much of the cream came off by rinsing with water after applying the cream on the hands. The oil resistance was evaluated by a sensory test of how much of the cream came off by applying an artificial sevum after applying the cream on the hands. The results are shown in Table 1.

TABLE 1

(Evaluation standards)
⊚: 15–20 panelers rated good.
○: 10–14 panelers rated good.
Δ: 5–9 panelers rated good.
x: 0–4 panelers rated good.

| | Example 1 | Comparative example 1 |
|---|---|---|
| Water resistance | ⊚ | ⊚ |
| Oil resistance | ⊚ | Δ |
| Long lasting cosmetic effect | ⊚ | Δ |

As clearly shown in Table 1, the cream of the present invention has a water resistance comparable to that of the cream of Comparative example and it is superior to Comparative example in terms of oil resistance and long lasting cosmetic effect.

(Comparative Example 2 Cream)

This cream was prepared in the same manner and with the same ingredients as in Example 1 except for the fact that the perfluoroalkyl modified methylphenyl polysiloxane (2) of Example 1 was replaced by a perfluoroalkyl denatured silicone compound represented by the following general formula (II) (X-22-821 from Shin-Etsu Chemical Co., Ltd.; Rf=$CF_3$, a=2, m=10–20 and n=30–40 in general formula (II)):

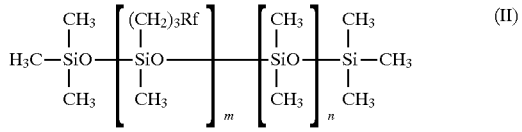

This cream was evaluated by a panel of 20 specialists As a result, all of the 20 panelists concluded that Example 1 of the present invention was superior in all aspects, i.e. water resistance, oil resistance and lasting cosmetic effect.

(Example 2 Foundation)

| | |
|---|---|
| (1) Titanium dioxide | 5.0% |
| (2) Talc | 10.0 |
| (3) Spherical polystyrene | 20.0 |
| (4) Mica | 43.0 |
| (5) Iron oxide | 7.0 |
| (6) Perfluoroalkyl denatured methylphenyl polysiloxane (L = 3, m = 100, n = 130, a = 3 and RF = $CF_3$ in general formula (I)) | 15.0 |
| (7) Preservative | Appropriate amount |
| (8) Antioxidant | Appropriate amount |
| (9) Perfume | Appropriate amount |

The materials (1)–(5) were mixed. Separately, the materials (6)–(9) were heated up to 80° C. and sprayed onto the mixture of the materials (1)–(5), followed by further mixing. After crushing and sifting, the product was molded in a pan by means of compression molding to obtain the foundation.

(Comparative example 3 Foundation)

| | |
|---|---|
| (1) Titanium dioxide | 5.0% |
| (2) Talc | 10.0 |
| (3) Spherical polystyrene | 20.0 |
| (4) Mica | 43.0 |
| (5) Iron oxide | 7.0 |
| (6) Dimethyl polysiloxane (300 CS/25° C.) | 15.0 |
| (7) Preservative | Appropriate amount |
| (8) Antioxidant | Appropriate amount |
| (9) Perfume | Appropriate amount |

Comparative example 3 was obtained in the same preparation method as Example 2.

(Effect)

Sensory testing of Example 2 and Comparative example 3 was conducted by a panel of 20 specialists in the same manner as in Example 1. The results are shown n Table 2.

TABLE 2

| | Example 2 | Comparative example 3 |
|---|---|---|
| Water resistance | ⊙ | ◯ |
| Oil resistance | ⊙ | Δ |
| Long lasting cosmetic effect | ⊙ | Δ |

As clearly shown in Table 2, the foundation of the present invention is superior in all aspects, i.e. water resistance, oil resistance and lasting cosmetic effect compared waspects, i.e. ith the comparative example.

(Comparative Example 4 Foundation)

A foundation was prepared in the same manner and with the same ingredients as in Example 2 except for the fact that the perfluoroalkyl denatured methylphenyl polysiloxane (6) of Example 2 was replaced by a perfluoroalkyl denatured silicone compound represented by the aforementioned general formula (II) (X-22-822 from Shin-Etsu Chemical Co., Ltd.; Rf=$CF_3$, a=2, m=15–25 and n=10–20 in general formula (II)). This foundation was evaluated by a panel of 20 specialists. As a result, all of the 20 panelists concluded that the foundation Example 2 of the present invention was superior in all aspects, i.e. water resistance, oil resistance and lasting cosmetic effect.

(Example 3 Cream)

| | |
|---|---|
| (1) Cetyl alcohol | 2.0% |
| (2) Stearyl alcohol | 1.5 |
| (3) Vaseline | 5.0 |
| (4) Squalane | 3.0 |
| (5) Jojoba oil | 3.0 |
| (6) Perfluoroalkyl denatured methylphenyl polysiloxane (l = 120, m = 60, n = 140, a = 8 and Rf = $C_{12}F_{25}$ in general formula (I)) | 2.0 |
| (7) Dimethyl polysiloxane (100 CS/25° C.) | 3.0 |
| (8) Glyceryl monostearate | 2.5 |
| (9) POE (5) glyceryl monostearate | 1.5 |
| (10) POE (25) cetyl ether | 3.0 |
| (11) Vitamin E acetate | 0.01 |
| (12) Preservative | 0.2 |
| (13) Dipropylene glycol | 2.0 |
| (14) Glycerine | 20.0 |
| (15) Purified water | 50.79 |

The materials (1)–(8) were heated and dissolved, and the temperature was kept at 70° C. to obtain the oil phase. Separately, the materials (9)–(15) were heated and dissolved, and the temperature was kept at 70° C. to obtain the water phase. The oil phase was added to the water phase and the mixture was thoroughly emulsified with an emulsifier. After the emulsification, the emulsion was cooled while being stirred. When the temperature became lower than 35° C., it was poured into a container and allowed to cool and harden. This cream was a cream superior in the long lasting cosmetic effect.

(Example 4 Hand lotion)

| | |
|---|---|
| (1) Dimethyl polysiloxane (5 CS/25° C.)) | 15.0% |
| (2) Perfluoroalkyl denatured methylphenyl polysiloxane (l = 22, m = 140, n = 4, a = 4 and Re = $C_4F_9$ in general formula (I)) | 80.0 |
| (3) Glyceryl triisostearate | 5.0 |

The materials (1)–(3) were mixed and stirred to obtain a hand lotion. This hand lotion was superior in terms of water resistance, oil resistance and long lasting cosmetic effect.

(Example 5 Sunscreen cosmetic)

| | |
|---|---|
| (1) Decamethyl cyclopentasiloxane | 48.0% |
| (2) Silicone resin | 5.0 |
| (3) Methylphenyl polysiloxane (20 CS/25° C.) | 10.0 |
| (4) 2-ethylhexyl-p-methoxycinnamate | 5.0 |
| (5) 4-t-butyl-4'-methoxybenzoyl methane | 2.0 |

| (Example 5 Sunscreen cosmetic) | |
| --- | --- |
| (6) Perfluoroalkyl denatured methylphenyl polysiloxane ($l = 12$, $m = 3$, $n = 8$, $a = 3$ and $Rf = C_8F_{17}$ in general formula (I)) | 30.0 |

The materials (1)–(6) were stirred and dissolved to obtain a sunscreen cosmetic. This sunscreen cosmetic was superior in terms of water resistance, oil resistance and long lasting cosmetic effect.

| (Example 6 Sunscreen lotion) | |
| --- | --- |
| (1) Dimethyl polysiloxane (6 CS/25° C.) | 19.0% |
| (2) Perfluoroalkyl denatured methylphenyl polysiloxane ($l = 36$, $m = 12$, $n = 48$, $a = 3$ and $Rf = C_6F_{12}$ in general formula (I)) | 5.0 |
| (3) Stearic acid | 1.0 |
| (4) 2-hydroxy-4-methoxybenzophenone | 3.0 |
| (5) Perfume | 0.2 |
| (6) Preservative | 0.2 |
| (7) Glycerine | 5.0 |
| (8) Montmorillonite | 0.5 |
| (9) Potassium hydroxide | 0.2 |
| (10) Purified water | 65.9 |

The materials (1)–(5) were mixed, heated and dissolved, and the temperature was kept at 70° C. to obtain the oil phase. Separately, the materials (6)–(10) were heated and dissolved, and the temperature was kept at 70° C. to obtain the water phase. The oil phase was added to the water phase and the mixture was thoroughly emulsified with an emulsifier. After the emulsification, the emulsion was cooled while being stirred to obtain a sunscreen lotion. This sunscreen lotion was superior in terms of water resistance, oil resistance and long lasting cosmetic effect.

| (Example 7 Emulsion) | |
| --- | --- |
| (1) Cetyl alcohol | 1.5% |
| (2) Perfluoroalkyl denatured methyl phenyl polysiloxane ($l = 1$, $m = 2$, $n = 7$, $a = 3$ and $Rf = C_8F_{17}$ in general formula (I)) | 6.0 |
| (3) Methylphenyl polysiloxane | 1.0 |
| (4) Glyceryl monooleate | 1.5 |
| (5) Glyceryl monostearate | 1.0 |
| (6) Perfume | 0.1 |
| (7) POE (20) sorbitan monostearate | 1.5 |
| (8) Preservative | 0.2 |
| (9) Carboxyvinyl polymer | 0.25 |
| (10) Triethanol amine | 0.1 |
| (11) 1,3-butylene glycol | 10.0 |
| (12) Purified water | 76.85 |

The materials (1)–(6) were mixed, heated and dissolved, and the temperature was kept at 70° C. to obtain the oil phase. Separately, the materials (7)–(12) were heated and dissolved, and the temperature was kept at 70° C. to obtain the water phase. The oil phase was added to the water phase and the mixture was thoroughly emulsified with an emulsifier. After the emulsification, the emulsion was cooled while being stirred to obtain the emulsion product. This emulsion was superior in terms of water resistance, oil resistance and long lasting cosmetic effect.

| Example 8 Eye shadow) | |
| --- | --- |
| (1) Titanium dioxide-coated mica | 44.5% |
| (2) Talc | 25.0 |
| (3) Ultramarine blue | 20.0 |
| (4) Red 226 | 0.5 |
| (5) Perfluoroalkyl denatured methylphenyl polysiloxane ($l = 8$, $m = 30$, $n = 80$, $a = 3$ and $Rf = C_8F_{17}$ in general formula (I)) | 10.0 |
| (6) Preservative | Appropriate amount |
| (7) Antioxidant | Appropriate amount |
| (8) Perfume | Appropriate amount |

The powder portion, prepared by thoroughly mixing the materials (1)–(4), was added to the materials (5)–(7) which had been heated and dissolved at 80° C. and thoroughly dispersed and mixed. The material (8) was then added and mixed into it. After deaeration, the mixture was put into a container to obtain an eye shadow. This eye shadow was superior in terms of water resistance, oil resistance and long lasting cosmetic effect.

| (Example 9 Oil-based foundation) | |
| --- | --- |
| (1) Mica | 20.5% |
| (2) Talc | 15.0 |
| (3) Kaolin | 10.0 |
| (4) Iron oxide | 4.0 |
| (5) Liquid paraffin | 35.0 |
| (6) Dimethyl polysiloxane | 8.0 |
| (7) Perfluoroalkyl denatured Methylphenyl polysiloxane ($l = 12$, $m = 20$, $n = 80$, $1 = 3$ and $Rf = C_8F_{17}$ in general formula (I)) | 5.0 |
| (8) Sorbitan sesquioleate | 2.0 |
| (10) Vitamin E | 0.5 |
| (10) Perfume | Appropriate amount |

The powder portion, prepared by mixing the materials (1)–(4), was added to the materials (5)–(10) which had been heated and dissolved at 90° C., and stirred and mixed with a homogenizer. After deaeration, the mixture was put into a container and cooled to obtain an oil-based foundation. This oil-based foundation was superior in terms of water resistance, oil resistance and long lasting cosmetic effect.

| (Example 10 Lipstick) | |
| --- | --- |
| (1) Solid paraffin | 15.0% |
| (2) Ceresin | 5.0 |
| (3) Dimethyl polysiloxane | 10.0 |
| (4) Perfluoroalkyl denatured methylphenyl polysiloxane ($l = 64$, $m = 20$, $n = 100$, $a = 3$ and $Rf = C_8F_{17}$ in general formula (I)) | 46.0 |
| (5) Red 201 | 1.5 |
| (6) Red 202 | 1.5 |
| (7) Titanium dioxide | 1.0 |
| (8) Titanium dioxide-coated mica | 20.0 |
| (9) Perfume | Appropriate amount |

The materials (1)–(4) and (9) were heated and dissolved, into which powder ingredients the materials (5)–(8) were mixed and thoroughly dispersed. After deaeration, the mixture was put into a prescribed metal mold and cooled to obtain a lipstick. This lipstick was superior in terms of long lasting cosmetic effect and gloss.

| (Example 11 Two way type foundation) | |
|---|---|
| (1) Silicone-treated mica | 35.0% |
| (2) Silicone-treated talc | 20.0 |
| (3) Fluorine-treated titanium dioxide | 5.0 |
| (4) Silicone-treated iron oxide | 5.0 |
| (5) Spherical nylon powder | 20.0 |
| (6) Perfluoroalkyl denatured methylphenyl polysiloxane ($l = 28$, $m = 13$, $n = 52$, $a = 3$ and $Rf = C_8F_{17}$ in general formula (I)) | 10.0 |
| (7) Dimethyl polysiloxane | 2.0 |
| (8) Liquid paraffin | 3.0 |
| (9) Preservative | Appropriate amount |
| (10) Antioxidant | Appropriate amount |
| (11) Perfume | Appropriate amount |

A two way type foundation was obtained in the same manner as in Example 2. This two way type foundation was superior in terms of water resistance, oil resistance and long lasting cosmetic effect.

| (Example 12 Hair foam) | |
|---|---|
| (1) Acrylic resin alkanolamine solution (50%) | 8.0% |
| (2) POE (60) hydrogenated castor oil | Appropriate amount |
| (3) Perfluoroalkyl denatured methylphenyl polysiloxane ($l = 28$, $m = 13$, $n = 52$, $a = 3$ and $Rf = C_8F_{17}$ in general formula (I)) | 5.0 |
| (4) Glycerine | 3.0 |
| (5) Preservative | Appropriate amount |
| (6) Perfume | Appropriate amount |
| (7) Purified water | 69.0 |
| (8) Ethyl alcohol | 15.0 |

The material (2) was dissolved in the material (4) and, after adding the material (3), the mixture was emulsified. Separately, the materials (1) and the materials (5)–(8) were stirred and mixed, and the previously prepared emulsion was added to it. Using this emulsion as a mother solution, 90% of the mother solution and 10% of liquified petroleum gas was put into a can to obtain a hair foam. This hair foam was superior in terms of long lasting cosmetic effect and gloss.

| (Example 13 Hair cream) | |
|---|---|
| (1) Liquid paraffin | 5.0% |
| (2) Perfluoroalkyl denatured methylphenyl polysiloxane ($l = 22$, $m = 20$, $n = 66$, $a = 3$ and $Rf = C_8F_{17}$ in general formula (I)) | 10.0 |
| (3) Vaseline | 15.0 |
| (4) Bees wax | 2.0 |
| (5) Preservative | Appropriate amount |
| (6) Perfume | Appropriate amount |
| (7) Purified water | 59.75 |
| (8) Carboxyvinyl polymer | 0.1 |
| (9) Xanthan gum | 0.1 |
| (10) Glycerine | 5.0 |
| (11) POE (60) hydrogenated castor oil | 3.0 |
| (12) Chelating agent | Appropriate amount |
| (13) Pigment | Appropriate amount |
| (14) Sodium hydroxide | 0.05 |

The materials (1)–(6) were heated and dissolved, and the temperature was kept at 80° C. to obtain the oil phase. The materials (7)–(13) were heated and dissolved, and the temperature was kept at 80° C. to obtain the water phase. The water phase was added to the oil phase while being stirred, and the mixture was thoroughly emulsified with an emulsifier. After the emulsion was cooled down to 30° C., the material (14) was added to it and stirring was done until the system was homogeneous. This hair cream was superior in terms of long lasting cosmetic effect and gloss.

What is claimed is:

1. A cosmetic which contains perfluoroalkyl denatured methylphenyl polysiloxane with a structure represented by the following formula (1):

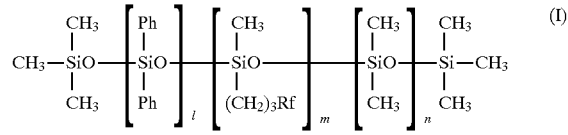

where l, m and n denote average numbers where l is 1–150, m is 1–150 and n is 0–150, a denotes an integer 0–10, and Rf denotes a perfluoroalkyl group with a carbon number of 1–12, in a cosmetically acceptable carrier.

* * * * *